(12) United States Patent
Perot et al.

(10) Patent No.: US 7,875,007 B2
(45) Date of Patent: Jan. 25, 2011

(54) SYRINGE ACCESSORY

(75) Inventors: Frederic Perot, Saint Paul de Varces (FR); Lionel Vedrine, Ridgewood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1296 days.

(21) Appl. No.: 10/520,980

(22) PCT Filed: Jul. 10, 2003

(86) PCT No.: PCT/FR03/02179

§ 371 (c)(1),
(2), (4) Date: Jul. 29, 2005

(87) PCT Pub. No.: WO2004/007006

PCT Pub. Date: Jan. 22, 2004

(65) Prior Publication Data

US 2006/0161114 A1    Jul. 20, 2006

(30) Foreign Application Priority Data

Jul. 12, 2002  (FR) .................................. 02 08845

(51) Int. Cl.
*A61M 5/00* (2006.01)
*A61M 5/31* (2006.01)
(52) U.S. Cl. ...................... 604/235; 604/240
(58) Field of Classification Search ............... 604/198, 604/232–5, 240–3, 224, 227, 228; 606/1, 606/92–4; 128/DIG. 1; 433/89, 90; 222/327, 222/325

See application file for complete search history.

(56) References Cited

U.S. PATENT DOCUMENTS

| 3,848,593 | A | * | 11/1974 | Baldwin ...................... 604/206 |
| 4,594,073 | A | * | 6/1986 | Stine .......................... 604/187 |
| 4,904,244 | A | | 2/1990 | Harsh et al. |
| 5,876,379 | A | | 3/1999 | Blatt et al. |
| 5,925,032 | A | | 7/1999 | Clements |
| 6,743,205 | B2 | * | 6/2004 | Nolan et al. ................. 604/154 |

FOREIGN PATENT DOCUMENTS

WO    WO 94/13347    6/1994

* cited by examiner

*Primary Examiner*—Kevin C Sirmons
*Assistant Examiner*—Catherine N Witczak
(74) *Attorney, Agent, or Firm*—David M. Fortunato; Cohen Pontani Lieberman & Pavane LLP

(57) ABSTRACT

According to the invention, the accessory (1) comprises a body (15) of roughly semi-tubular shape, first means of holding the syringe comprising a distal transverse wall (20) connected to one end of said body (15), and pierced with a hole (22) for the passage of the needle (7) through it, and second means of holding the syringe comprising a bearing zone (61) against which the proximal flange (10) or the lateral lugs that the syringe body (5) comprises is or are intended to bear so as to provide support for the user's fingers; the distance between said distal transverse wall (20) and said bearing zone (61) is such that the adapter (8) connecting the needle (7) to the syringe body (5) is kept bearing against said distal transverse wall (20) when said flange (10) or said lateral lugs are bearing against said bearing zone (61).

22 Claims, 3 Drawing Sheets

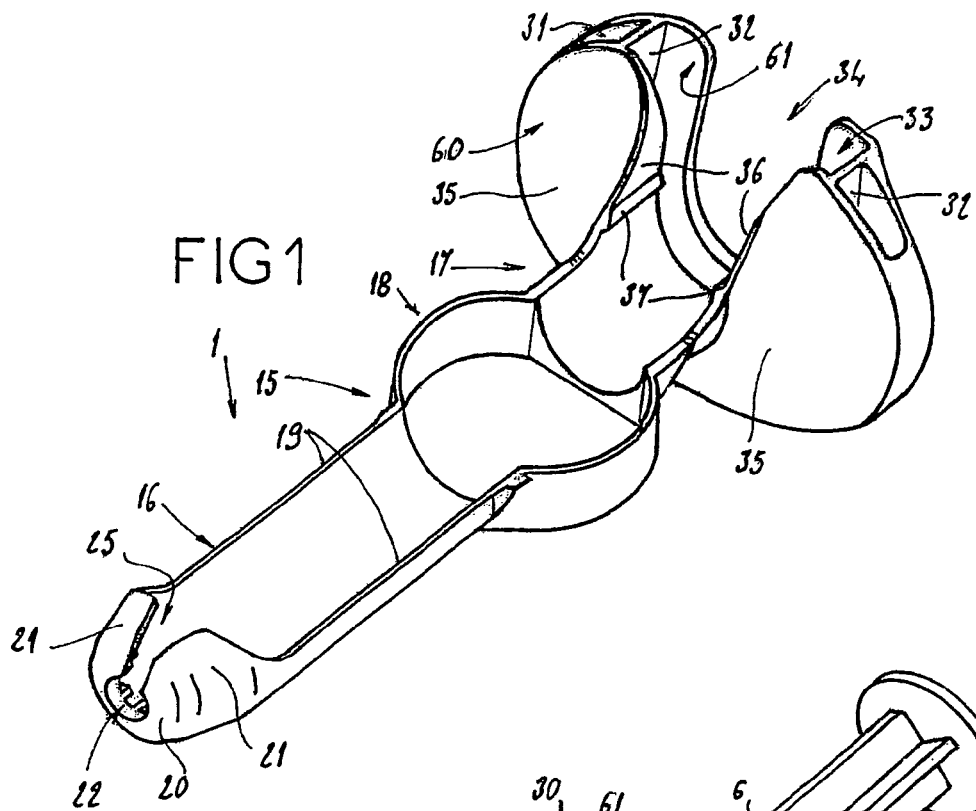
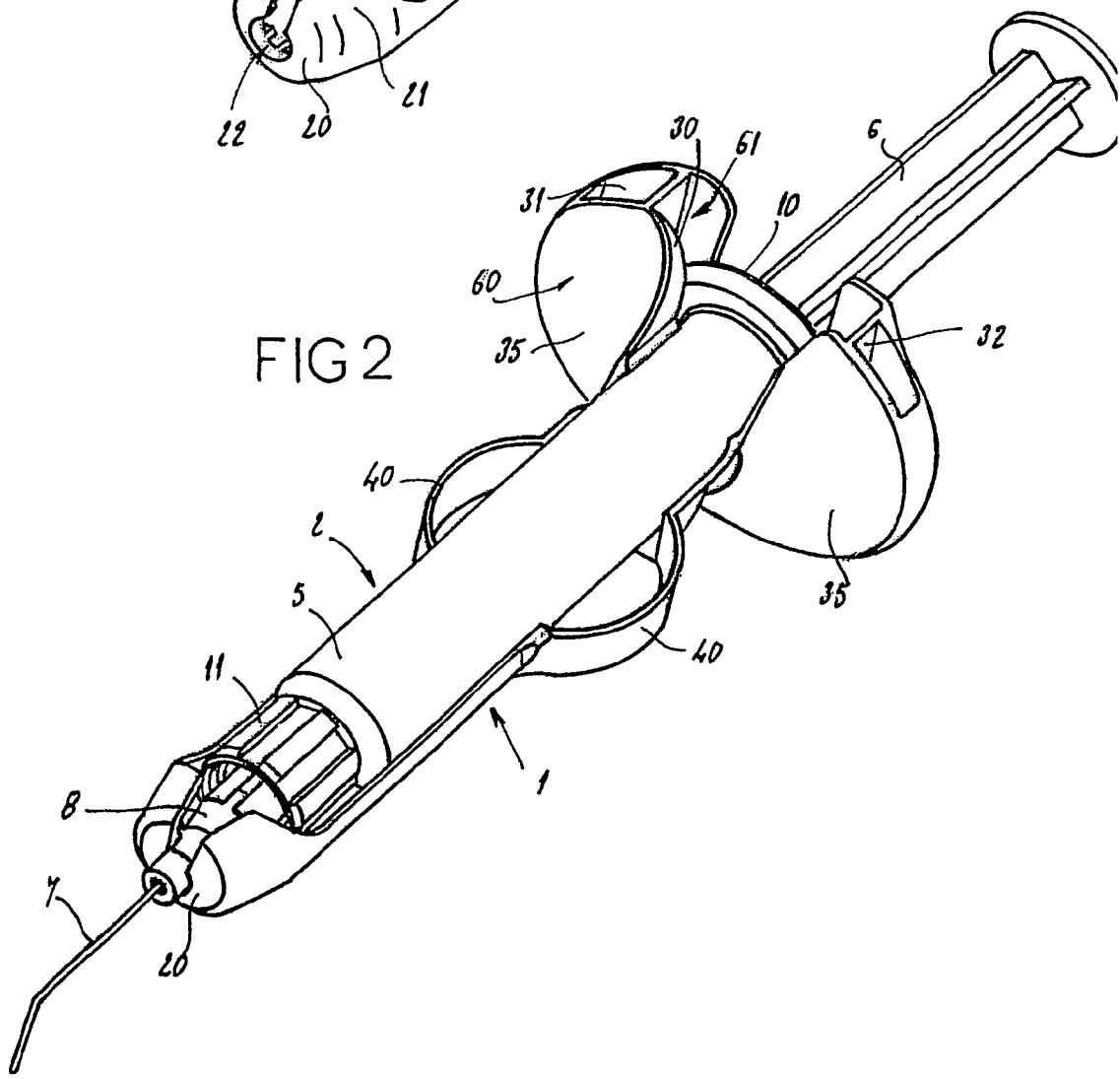

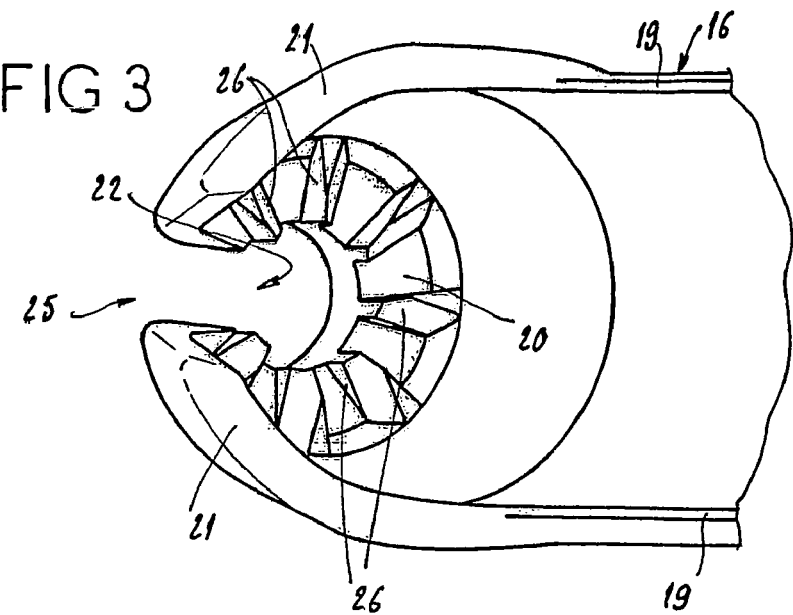
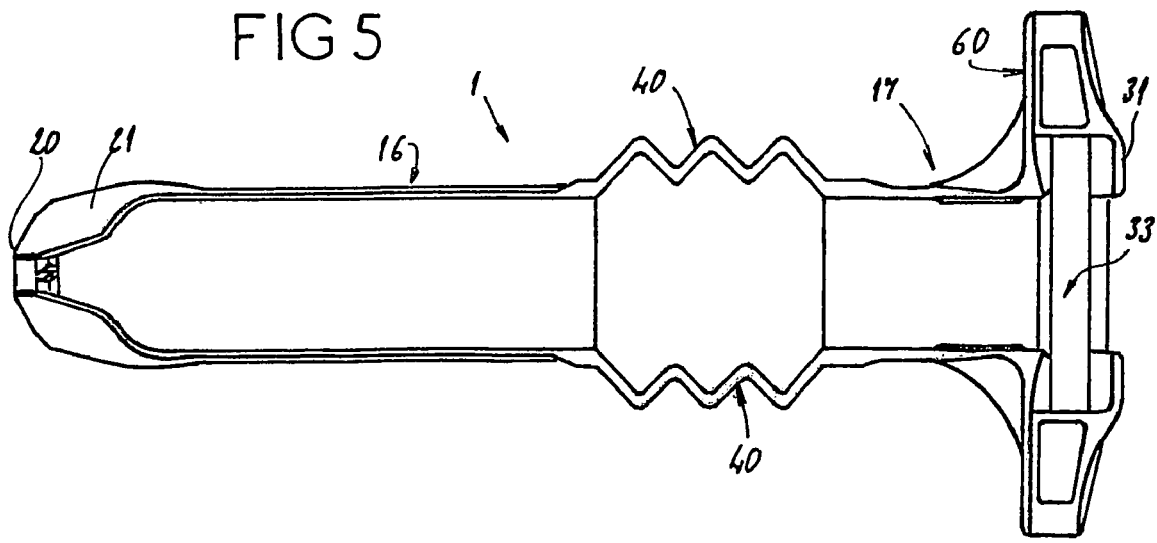

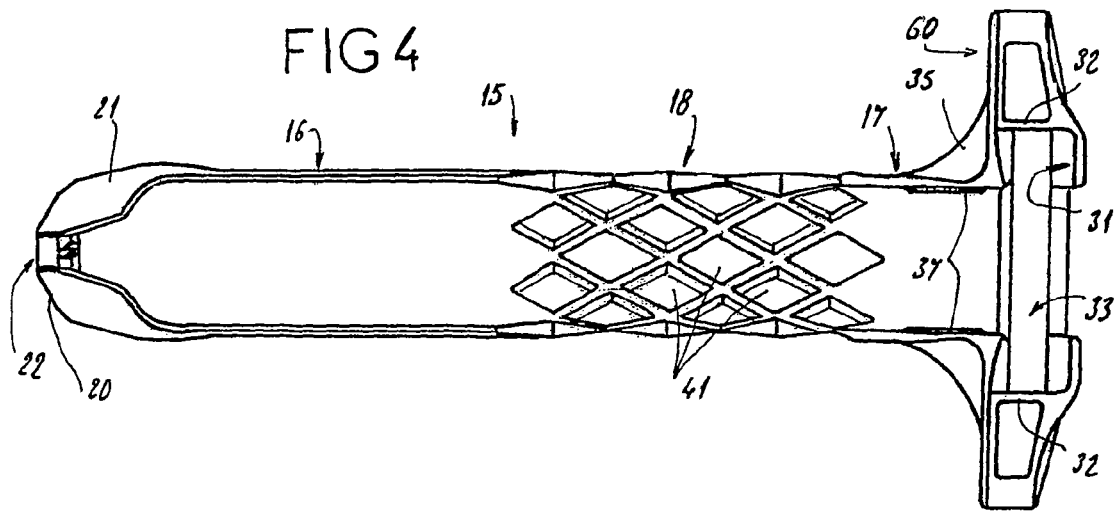
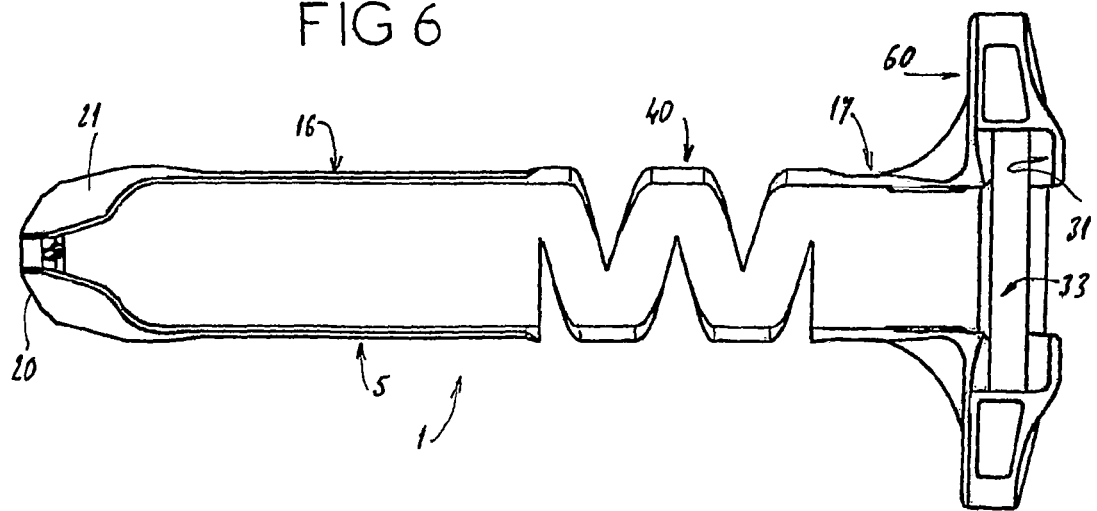

SYRINGE ACCESSORY

The present invention relates to an accessory for a syringe.

BACKGROUND OF THE INVENTION

In certain cases, an injection performed using a syringe has the effect of generating longitudinal stress in the needle at the time of injection. There is a risk that this stress will cause the needle and/or its connecting adapter to separate from the syringe body during the injection. This is particular the case when it is necessary to inject a viscous product.

A screw connection known as a "luer-lock" connection partially solves this problem but is not in any way capable of preventing the needle from becoming unscrewed under said stress. Such unscrewing, even partial, may cause lesions in the surrounding tissue, as much as a result of the injection of the product as of the unwanted movement of the needle, particularly when this needle is curved or bent. This problem arises particularly in the field of ophthalmic surgery, in which viscous products and curved needles are used.

DESCRIPTION OF THE PRIOR ART

There does exist an accessory for a syringe particularly used in ophthalmic surgery, comprising a tubular element, a nut and a retaining ring. The tubular element is intended internally to accommodate a syringe body and forms a distal external screw thread. The nut has a bottom pierced with a hole and is intended to be fitted over the needle by virtue of this hole, then to be screwed onto the screw thread of the tubular element until its bottom bears against the needle connecting adapter, thus retaining the needle with respect to the syringe body. The retaining ring, for its part, holds the syringe body in the tubular element.

The disadvantage of this accessory is that it makes it possible for the needle to become damaged or contaminated while the nut is being fitted. In addition, it has a relatively complex structure and entails preloading the syringe in the tubular element, something which is relatively tricky to do, and is not without influence on the cost of its manufacture and of its use.

The object of the invention is to remedy these disadvantages.

The accessory to which the invention relates comprises, in a way known per se, a body, first holding means bearing against the needle of the syringe or against the adapter that connects this needle to this syringe, and second holding means bearing against the syringe body, these first and second holding means allowing the needle to be held on the syringe body when stress is exerted on the needle in the longitudinal direction of the syringe at the time of injection, with a tendency to separate the needle from the syringe body.

According to the invention,
the body of the accessory is of roughly semi-tubular shape;
said first holding means comprise a distal transverse wall connected to one end of said body and pierced with a hole for the passage of the needle through it, and
said second holding means comprise a bearing zone against which the proximal end of the syringe body is intended to bear,
the distance between said distal transverse wall and said bearing zone being such that the adapter connecting the needle to the syringe body is kept bearing against said distal transverse wall when the syringe body bears against said bearing zone.

On account of its shape, the body of the accessory allows quick and easy engagement of the syringe into it, and said distal transverse wall eliminates the engaging of a nut over the needle, and therefore the risk of damaging or contaminating this needle during this engagement. In addition and furthermore, the bearing of the connecting adapter against said distal transverse wall generates friction between this adapter and this wall, and this is able to prevent the needle from pivoting when the latter is connected to the syringe body by a screwed connection, particularly of the "leur-lock" type, under said longitudinal stress.

As a preference, the body of the accessory consists in a semi-tube.

As a preference, the accessory comprises at least one means allowing the needle adapter to be prevented from rotating with respect to the body of the accessory.

This prevention of rotation makes it possible to fix the needle adapter in terms of rotation when this adapter is connected to the syringe body by a screw connection, particularly of the "leur-lock" type.

This rotation-preventing means may in particular be in the form of at least one tooth projecting from said distal transverse wall and/or of a rim contiguous therewith, which is intended to collaborate with at least one rib that the adapter for connecting the needle to the syringe body often has.

When the accessory comprises several of these teeth, the teeth may in particular be arranged around the hole that said distal transverse wall comprises for allowing the passage of the needle, in a radial direction with respect to this hole.

As an alternative to these rotation-prevention means, or in addition to them, the adapter may have a more or less conical or cylindro-conical shape and be intended to be jammed into said hole in said transverse wall.

The accessory is advantageously made as a single piece, particularly by molding in a synthetic material.

It may thus be manufactured at a low cost price.

Advantageously, said body of the accessory is made in two parts, one of which comprises said distal transverse wall and the other of which comprises said bearing zone, these two parts being connected to one another by an elastic zone that can be stretched in the longitudinal direction of the accessory.

This elastic zone allows the accessory to be fitted to syringe bodies of different lengths or to suit the manufacturing or assembly tolerances that syringe bodies of standard length assembled with a needle may exhibit.

Said elastic zone may in particular comprise at least one curved, perforated, undulating or helicoid portion connecting said parts of the body of the accessory.

As a preference, the aforementioned hole that said distal transverse wall comprises for the passage of the needle opens to the outside of this wall via at least one slot, this slot allowing the needle to be engaged in said hole laterally.

This engagement is thus easy and able to preserve the integrity of the distal end of the needle. It can be performed at the same time as the syringe body is engaged in said body of the accessory, in the same action.

Said bearing zone of the proximal end of the syringe body may be shaped to form a stop allowing the piston plunger to slide, but lying in the return path of the piston of the syringe or part of the piston plunger.

The accessory thus prevents the piston from leaving the syringe body.

Said bearing zone may be delimited by at least a proximal transverse wall that it has. According to a preferred embodiment of the invention, in this case, the accessory comprises two roughly parallel proximal transverse walls offset in the longitudinal direction and which between them delimit a housing for accommodating the proximal flange or proximal lateral tabs that the body of the syringe might have.

This housing may be tailored to said proximal flange or these proximal lateral tabs so as to mount the accessory on the syringe through friction.

This housing preferably opens laterally in roughly the same direction as the direction in which said hole for the passage of the needle communicates with the outside of the accessory via said slot.

It is thus easier to engage the syringe in the accessory.

Alternatively or in addition, the accessory may be mounted on the syringe by snap-fitting the syringe into the accessory, the latter comprising means for that purpose.

The accessory may also comprise a connecting wall which, at its face facing toward the distal transverse wall intended to accommodate the adapter for connecting the needle, forms lateral surfaces on each side of the body of the accessory, these lateral surfaces being intended to accommodate the user's fingers and being shaped ergonomically for that purpose.

The body of the accessory may have two longitudinal edges delimiting the housing that accommodates the syringe body, these edges having shapes which taper toward their free edges in order to facilitate use of the accessory in combination with the syringe.

BRIEF DESCRIPTION OF THE DRAWINGS

For a good understanding thereof, the invention is described once again hereinbelow with reference to the appended schematic drawing which, by way of nonlimiting example, depicts one preferred embodiment of the accessory for a syringe to which it relates.

FIG. 1 is a perspective view thereof;

FIG. 2 is a perspective view thereof, after a syringe has been fitted on it;

FIG. 3 is a partial view thereof, in perspective and on a larger scale, and

FIGS. 4 to 6 are side views of various alternative forms of embodiment of the accessory.

DESCRIPTION OF THE PREFERRED EMBODIMENTS

The parts or elements of the accessory shown in FIGS. 1 to 3, which are found again identically or similarly in the various alternative forms of embodiment will be referenced with the same numerical references and will not be described again.

FIG. 1 depicts an accessory 1 for a syringe and FIG. 2 depicts a syringe 2 fitted into this accessory 1.

This syringe 2, particularly intended to be used in the field of ophthalmic surgery, is of conventional type, comprising a syringe body 5, a piston actuated by a plunger 6, a needle 7 and an adapter 8 for connecting the needle 7 to the syringe body 5.

The latter comprises a proximal flange 10 and, at the opposite end to this flange 10, a distal adapter, not visible in the figures, for connecting the adapter 8 to the needle 7.

The needle 7 is bent in the example depicted, as may be used in the field of ophthalmic surgery.

The connecting adapter 8 has a more or less conical or cylindro-conical shape and comprises ribs (not visible in FIG. 2) protruding from its wall at its distal end. In the example depicted, it collaborates with a nut 11, of the "luer-lock" type, allowing the adapter 8 to be connected to the syringe body 5 by screwing the adapter 8 into this nut 11.

With reference to FIG. 1, it can be seen that the accessory 1 comprises a body 15 made in two parts 16, 17 joined together by an elastic zone 18 which can be stretched elastically.

The body 15 has a semi-cylindrical shape and is shaped to envelop practically half of the syringe body 5. It has two longitudinal edges 19 delimiting the housing that accommodates the syringe body 5, these edges 19 having shapes which taper toward their free edges so as to make the accessory with the syringe easier for the user (surgeon) to use.

The part 16 has a distal transverse wall 20, bordered by a semi-peripheral lateral rim 21, in which a hole 22 is made for the passage of the needle 7. In the example depicted, this hole 22 is sized to accommodate the distal end of the adapter 8 so that the latter is jammed in, bearing in mind the somewhat conical shape of this adapter 8.

In the example depicted, the hole 22 communicates with the outside of the accessory 1 via a slot 25 allowing the needle 7 to be engaged through it, laterally with respect to the accessory 1, when the syringe 2 is being fitted into the accessory 1.

Furthermore, as shown in FIG. 3, the distal transverse wall 20 and the rim 21 comprise teeth 26 projecting from its proximal face, arranged around the hole 22 in a radial orientation with respect to this hole 22. These teeth 26 are intended to collaborate with the aforementioned ribs that the adapter 8 has.

The part 17 comprises two roughly parallel proximal transverse walls 30, 31 which are offset in the longitudinal direction of the accessory 1, and possibly two stiffening partitions 32. The walls 30, 31 together form a bearing zone 61 and between them delimit a housing 33 intended to accommodate the flange 10, and have two notches 34 respectively accommodating the tubular part of the syringe body 5 and the piston plunger 6, as shown in FIG. 2. These notches 34 are directed roughly in the same direction as the slot 25.

At the entries to these notches 34, the walls 30, 31 are flared, so as to make it easier for the proximal part of the syringe 2, the piston plunger 6 and, in particular, the flange 10, to be engaged in the housing 33. In the case of the use of a "carpule" instead of a syringe, these same proximal transverse walls 30 and 31 make it easier for just the proximal end of the body of the carpule and for the piston plunger to enter.

A connecting wall 60 may also have lateral surfaces 35, on each side of the body 15 of the accessory 1. These surfaces 35 are intended to receive the user's fingers and are shaped ergonomically for that purpose.

The part 17 also comprises two parallel longitudinal walls 36 contiguous to the connecting wall 60, which extend the edges of the body 15. At least one of these walls comprises at least one rib 37 for snap-fitting the syringe body 5 into this body 15.

The elastic zone 18 comprises two curved portions 40 the complex faces of which face toward the outside of the accessory 1. These curved portions 40 allow the accessory 1 to be adapted either to suit syringe bodies 5 of different lengths or to suit the manufacturing tolerances that may be exhibited by syringe bodies 5 of standard length, and the assembly of a needle 7/adapter 8 with a syringe body 5 placed in the accessory 1.

FIGS. 4 to 6 respectively show that the elastic zone 18 may be formed by perforations 41 formed in the body 15 or that it may have undulating portions 40 or a semi-helicoid portion 40.

It is evident from the foregoing that the invention affords a definite improvement to the prior art, by providing an accessory for a syringe which does not expose the needle to a risk of damage or contamination during its use, and which has a structure which is simple and inexpensive to manufacture, which does not entail the manufacturer or a third-party pre-loading the syringe into the accessory.

It goes without saying that the invention is not restricted to the form of embodiment described hereinabove by way of example but that, on the contrary, it encompasses all alternative forms of embodiment thereof which are covered by the claims attached hereto; thus, the product contained in the syringe may not be viscous, the needle may not be curved, the needle may not be connected by a "leur-lock" connection, the accessory may accommodate either empty or pre-filled syringes, the hole 22 may communicate with the outside of the accessory 1 via one or more slots 25; the term syringe is to be understood in the broadest sense as including similar containers commonly known as "carpules" or "cartridges", that is to say with bodies 5 with no flange 10 or with just a rim, comprising a piston for driving the liquid contained in said body.

The field of application of the present invention is not restricted to that of ophthalmic surgery, but may be extended to cover many other fields of medicine such as that of dental care with the use of an anesthetic, etc.

The invention claimed is:

1. An accessory for a syringe, the syringe having a syringe body with a proximal end having a flange and a distal end for supporting a needle at the distal end by way of an adapter, the accessory comprising:

an accessory body having a longitudinal axis, a distal end and a proximal end, the accessory body having an elastic zone arranged between the distal end and the proximal end coupling the distal end and the proximal end, the elastic zone being configured to expand elastically in the longitudinal direction of the accessory from a first, rest position, to a second position where a distance between the distal and proximal ends is increased;

a first holding means positioned at the distal end of the accessory body and having a wall configured for receiving the adapter; a distal part connecting the first holding means to the elastic zone;

a second holding means positioned at the proximal end of the accessory body and having structure configured for receiving the flange; and a proximal part connecting the second holding means to the elastic zone; whereby the elastic zone forms a part of the distal and proximal parts, and when the elastic zone is in the first position, the flange is secured by the second holding means and the adapter is secured by the first holding means so that the syringe is secured to the accessory, and whereby when the elastic zone is in the second position, the adaptor is movable away from the first holding means.

2. The accessory as claimed in claim 1, further comprising at least one means for preventing the adapter from rotating with respect to the accessory body.

3. The accessory as claimed in claim 2, wherein said rotation-preventing means comprises at least one tooth projecting from the first holding means.

4. The accessory as claimed in claim 3, wherein the wall of the first holding means defines a hole for receiving the needle therein and wherein said at least one tooth comprises several teeth arranged around the hole.

5. The accessory as claimed in claim 4, wherein the adapter has a conical shape dimensioned for being received in said hole.

6. The accessory as claimed in claim 1, wherein the body is integrally formed by molding in a synthetic material.

7. The accessory as claimed in claim 1, wherein said elastic zone comprises at least one of a curved, perforated, undulating and helicoid portion.

8. The accessory as claimed in claim 7, wherein a hole configured for the passage of the needle opens to an outside of the wall of the first holding means via at least one slot, this slot allowing the needle to be engaged in the hole laterally.

9. The accessory as claimed in claim 8, wherein a bearing zone is shaped to form a stop allowing a piston plunger to slide but lying in a return path of the piston of the syringe or part of the piston plunger.

10. The accessory as claimed in claim 9, wherein said bearing zone is delimited by at least one proximal transverse wall.

11. The accessory as claimed in claim 10, and which comprises two roughly parallel proximal transverse walls offset in the longitudinal direction and which between them delimit a housing for accommodating a proximal flange or proximal lateral tabs of the body of the syringe.

12. The accessory as claimed in claim 11, wherein said housing is tailored to said proximal flange or said proximal lateral tabs.

13. The accessory as claimed in claim 12, wherein said housing opens laterally in roughly the same direction as the direction in which said hole for the passage of the needle communicates with the outside of the accessory via said slot.

14. The accessory as claimed in claim 13, and which comprises means for snap-fastening the syringe into it.

15. The accessory as claimed in claim 14, and which comprises a connecting wall which, at its face facing toward the wall of the first retaining means, forms lateral surfaces on each side of the body of the accessory, these lateral surfaces being intended to accommodate the user's fingers and being shaped ergonomically for that purpose.

16. The accessory as claimed in claim 15, and of which the body has two longitudinal edges delimiting a housing that accommodates the syringe body, these edges having shapes which taper toward their free edges.

17. The accessory as claimed in claim 16, and which is designed for a container being one of a carpule or cartridge type.

18. The accessory as claimed in claim 1, wherein said accessory body is a semi-tube.

19. An accessory for a syringe, the syringe having a syringe body with a proximal end having a flange and a distal end for supporting a needle at the distal end by way of an adapter, the accessory comprising:

an accessory body having a longitudinal axis, a distal end and a proximal end, the accessory body having an elastic zone arranged between the distal end and the proximal end coupling the distal end and the proximal end, the elastic zone being configured to expand elastically in the longitudinal direction of the accessory from a first, rest position, to a second position where a distance between the distal and proximal ends is increased;

a wall positioned at the distal end of the accessory body and being configured for receiving the adapter; a distal part connecting the wall to the elastic zone;

a housing positioned at the proximal end of the accessory body and being configured for receiving the flange; and a proximal part connecting the housing to the elastic zone; whereby the elastic zone forms a part of the distal and proximal parts, and when the elastic zone is in the first position, the flange is secured by the housing and the adapter is secured by the wall so that the syringe is secured to the accessory, and whereby when the elastic zone is in the second position, the adaptor is movable away from the wall.

20. The accessory as claimed in claim 19, further comprising at least one projection configured to prevent the adapter from rotating with respect to the accessory body.

21. The accessory as claimed in claim 20, wherein said projection comprises at least one tooth projecting from the wall.

22. The accessory as claimed in claim 21, wherein the wall defines a hole for receiving the needle therein and wherein said at least one tooth comprises several teeth arranged around the hole.

* * * * *